United States Patent [19]

Derian et al.

[11] Patent Number: 5,334,585
[45] Date of Patent: Aug. 2, 1994

[54] PYRETHROID MICROEMULSION COMPOSITIONS AND METHOD FOR CONTROLLING INSECTS THEREWITH

[75] Inventors: Paul-Joel Derian, Sceaux; Gilles Guerin, Eaubonne, both of France

[73] Assignee: Rhone-Poulenc Chimie, Courbevoie, France

[21] Appl. No.: 838,669

[22] Filed: Feb. 21, 1992

[30] Foreign Application Priority Data

Feb. 22, 1991 [FR] France .................. 91 02374

[51] Int. Cl.$^5$ ................ A01N 65/00; A01N 37/34
[52] U.S. Cl. ........................ 514/74; 514/65; 514/71; 514/72; 514/73; 514/941; 514/942; 514/521; 424/195.1; 71/DIG. 1
[58] Field of Search ............... 252/312; 514/521, 941, 514/942, 71, 72, 73, 74; 71/DIG. 1

[56] References Cited

U.S. PATENT DOCUMENTS

| | | |
|---|---|---|
| 2,719,785 | 10/1955 | Johnson . |
| 4,461,641 | 7/1984 | Abildt et al. ............... 71/93 |
| 4,500,348 | 2/1985 | Hausmann et al. ............. 71/103 |
| 4,536,301 | 8/1985 | Malloy et al. ............. 252/8.554 |
| 4,745,114 | 5/1988 | Elliott et al. ............. 514/233.5 |
| 4,861,367 | 8/1989 | Nyfeler et al. ............. 71/92 |
| 4,870,103 | 9/1989 | Röechling et al. ............. 514/521 |
| 4,904,695 | 2/1990 | Bell ............. 514/521 |
| 4,954,338 | 9/1990 | Mattox ............. 424/78 |
| 5,028,623 | 7/1991 | Matsunaga et al. ............. 514/521 |
| 5,082,591 | 1/1992 | Marchetto et al. ............. 252/312 X |
| 5,154,754 | 10/1992 | Damó et al. ............. 71/DIG. 1 |

FOREIGN PATENT DOCUMENTS

| | | |
|---|---|---|
| 1209361 | 8/1986 | Canada . |
| 0062181 | 10/1982 | European Pat. Off. . |
| 0088049 | 9/1983 | European Pat. Off. . |
| 0107009 | 5/1984 | European Pat. Off. . |
| 0160182 | 11/1985 | European Pat. Off. . |
| 0297207 | 1/1989 | European Pat. Off. . |
| 0302701 | 2/1989 | European Pat. Off. . |
| 0432062 | 6/1991 | European Pat. Off. . |
| 2634974 | 2/1990 | France . |

*Primary Examiner*—Richard D. Lovering
*Attorney, Agent, or Firm*—Finnegan, Henderson, Farabow, Garrett & Dunner

[57] ABSTRACT

Stable pyrethroid microemulsion compositions having from 0.1% to 95% by weight/weight of at least one pyrethroid in liquid form; from 2% to 90% by weight/weight of a three-component surfactant system having at least one anionic surfactant, at least one nonionic surfactant and at least one co-surfactant chosen from aliphatic alcohols, cycloaliphatic alcohols, arylaliphatic alcohols, ether-alcohols and aliphatic carboxylic acids; and water.

The ratio by weight of anionic surfactant/nonionic surfactant is from 10/90 to 90/10, and the ratio by weight of co-surfactant/anionic and nonionic surfactants is from 0.1 to 1.5.

The microemulsion compositions are applied directly or after dilution with water to plants (crops) or wood for controlling insects.

19 Claims, No Drawings

PYRETHROID MICROEMULSION COMPOSITIONS AND METHOD FOR CONTROLLING INSECTS THEREWITH

BACKGROUND OF THE INVENTION

The present invention relates to novel, stable microemulsion compositions and to a method for controlling insects therewith, and more particularly to novel, stable microemulsion compositions of pyrethroids and to a method for controlling insects therewith.

Insecticides are commonly formulated as dusts, water dispersions, emulsions and solutions. It is well-known in the prior art that the preparation and use of such formulations involves accessory agents, such as dust carriers, solvents, emulsifiers, wetting and dispersing agents, stickers and deodorants or masking agents and the like, depending upon the particular formulation chosen for the insecticide.

The successful employment of any insecticide depends upon its proper formulation in a preparation that can be applied for insect control with safety to the applicator, animals and plants without compromising the effectiveness of the insecticide in controlling a particular insect or insects.

As indicated above, emulsions are commonly used in formulating insecticide compositions. However, it is well-known in the art that emulsions are frequently unstable systems and that the risk of deterioration, e.g., separation, of the ingredients in the emulsion during storage is greater than with a non-emulsified product.

Pyrethroids are well-known insecticidal compounds which may be used to control insects, particularly in the protection of plants or of wood. In many instances, it is desirable to apply pyrethroids to plants or wood in the form of emulsions. Whether the pyrethroids are formulated for direct use or for storage and subsequent use, it is desirable to formulate emulsions of pyrethroids which will not have any of the above disadvantages, will remain stable during storage and use, and will be effective in controlling insects in the treatment of crops and the protection of wood.

SUMMARY OF THE INVENTION

In accordance with the present invention, it has been found that highly stable, pyrethroid microemulsion compositions can be prepared by forming the microemulsion of pyrethroid in an aqueous surfactant system. The surfactant system must include at least one anionic surfactant, at least one nonionic surfactant and at least one co-surfactant.

More precisely, the present invention relates to stable pyrethroid microemulsion compositions having from 0.1% to 95% by weight/weight of at least one pyrethroid in liquid form; from 2% to 90% by weight/weight of a surfactant system of (a) at least one anionic surfactant chosen from neutral phosphates or sulfates of alkoxylated di(1-phenylethyl)phenols or alkoxylated tri (1-phenylethyl) phenols, or alkali metal, alkaline earth metal, ammonium, alkylammonium and/or cycloalkylammonium or alkanolantmonium alkylbenzenesulfonates; (b) at least one nonionic surfactant chosen from alkoxylated di (1-phenylethyl)phenols, alkoxylated tri (1-phenylethyl)phenols or ethoxypropoxylated straight-chain or branched aliphatic alcohols having from 3 to 10 carbon atoms, cycloaliphatic alcohols having from 5 to 12 carbon atoms, arylaliphatic alcohols having from 7 to 12 carbon atoms, ether-alcohols of the formula R—(OR')$_n$—OH, in which R represents a straight-chain or branched alkyl radical having from 1 to 8 carbon atoms, R' represents an alkylene radical, such as, for example, ethylene or propylene, and n represents an integer from 1 to 3, or straight-chain or branched aliphatic carboxylic acids having from 5 to 10 carbon atoms; and water; wherein the ratio by weight of anionic surfactant/nonionic surfactant is from 10/90 to 90/10, and the ratio by weight of co-surfactant/anionic and nonionic surfactants is from 0.1 to 1.5.

DETAILED DESCRIPTION OF THE INVENTION

As indicated above, pyrethroids are well-known in the art and are insecticidal compounds which may be used, in particular, in protecting plants or wood from insects. The following are examples of some of the best known pyrethroids which may be used in the compositions and method of the present invention. The pyrethroids include allethrin, bifenthrin, bioallethrin, bioresmethrin, cyfluthrin, cyhallothrin, cypermethrin, deltamethrin, fenpropathrin, permethrin, phenothrin, pyrethrins, resmethrin, tefluthrin, tetramethrin, tralomethrin, (E)-5-benzyl-3-furylmethyl-(1R)-cis-2,2-dimethyl-3-(2-oxothiolan-3-ylidene-methyl) cyclopropanecarboxylate and the like. The foregoing examples of pyrethroids are not meant to be limiting in scope in the present invention, and it is within the scope of the present invention to use other pyrethroids which can be formed into stable microemulsion compositions in accordance with the present invention.

The pyrethroids may be used as such, in particular those which are liquid at ambient temperature, that is to say at about 10° to 25° C., or those which may be supercooled.

It is also possible to use the pyrethroids in solution in an organic solvent which is insoluble in water (or in a mixture of such organic solvents), in particular, the pyrethroids which have a melting point higher than about 50° C., without this temperature being a critical limitation on the pyrethroids which may be used in the compositions of the present invention.

The following organic solvents which enable the pyrethroids to be maintained and used in the liquid state include, for example, aromatic hydrocarbons, such as benzene, toluene or xylenes; aromatic petroleum cuts; fatty acid alkyl esters, such as methyl oleate; dialkyl phthalates, such as di (2-ethylhexyl) phthalate; chlorinated hydrocarbons, such as dichloromethane, trichloromethane or 1,2-chloroethane; and cyclic ketones, such as cyclopentanone, cyclohexanone or isophorone.

When an organic solvent is used, the ratio by weight of organic solvent/pyrethroid may vary widely from 5/95 to 90/10.

In the present text the term "pyrethroid in liquid form" thus encompasses liquid, supercooled or dissolved pyrethroids. In this latter case, the amounts of pyrethroid expressed in the formulations comprise both the pyrethroid itself and the solvent in which it is dissolved.

One pyrethroid or a mixture of two or more pyrethroids may be used in the microemulsion compositions of the present invention.

The anionic surfactants used in the pyrethroid microemulsion compositions of the present invention include, for example, phosphoric monoesters and diesters of ethoxylated di(1-phenylethyl )phenols containing from 2 to 50 ethylene oxide (EO) units, phosphoric monoesters and diesters of ethoxylated tri(1-phenylethyl)-phenols containing from 2 to 50 EO units, phosphoric monoesters and diesters of propoxylated di(1-phenylethyl)phenols containing from 2 to 50 propylene oxide (PO) units, phosphoric monoesters and diesters of propoxylated tri(1-phenylethyl)phenols containing from 2 to 50 PO units, phosphoric monoesters and diesters of ethoxypropoxylated di(1-phenylethyl) phenols containing from 2 to 50 EO + PO units, phosphoric monoesters and diesters of ethoxypropoxylated tri(1-phenylethyl)phenols containing from 2 to 50 EO + PO units, sulfuric monoesters and diesters of ethoxylated di(1-phenylethyl)phenols containing from 2 to 50 EO units, sulfuric monoesters and diesters of propoxylated di(1-phenylethyl) phenols containing from 2 to 50 PO units, sulfuric monoesters and diesters of ethoxypropoxylated di(1-phenylethyl)phenols containing from 2 to 50 EO + PO units, sulfuric monoesters and diesters of ethoxylated tri ( 1-phenylethyl )phenols containing from 2 to 50 EO units, sulfuric monoesters and diesters of propoxylated tri(1-phenylethyl)phenols containing from 2 to 50 PO units, sulfuric monoesters and diesters of ethoxypropoxylated tri(1-phenylethyl)phenols containing from 2 to 50 EO + PO units and the like, in which any free acid groups are neutralized by alkanolamines or ammonium, potassium or sodium cations, and sodium, potassium, calcium, ammonium, diethanolammonium, triethanolammonium and N-methylcyclohexylammonium nonylbenzenesulfonates and dodecylbenzenesulfonates.

Examples of anionic surfactants which may be used in a nonlimiting manner in the compositions of the present invention, are such compounds as, triethanolamine salts of the phosphoric monoester and diester of ethoxylated tri(1-phenylethyl )phenol containing 16 EO units, the potassium salts of the phosphoric monoester and diester of ethoxylated tri( 1-phenylethyl )phenol containing 16 EO units, the potassium salt of the sulfuric monoester of the ethoxylated di(1-phenylethyl)phenol containing 15 EO units, the triethanolamine salt of the sulfuric monoester of ethoxylated di ( 1-phenylethyl )phenol containing 11 EO units, the ammonium salt of the sulfuric monoester of ethoxylated tri(1-phenylethyl )phenol containing 16 EO units, the ammonium salt of the sulfuric monoester of ethoxylated di (1-phenylethyl)-phenol containing 5 EO units, the ammonium salt of the sulfuric monoester of ethoxylated di(1-phenylethyl)-phenol containing 7 EO units, the ammonium salt of the sulfuric monoester of ethoxylated di(1-phenylethyl)-phenol containing 11 EO units, calcium dodecylbenzenesulfonate, ammonium dodecylbenzenesulfonate, sodium dodecylbenzenesulfonate, potassium dodecylbenzenesulfonate, triethanolammonium dodecylbenzenesulfonate and the like.

It is, of course, possible to use mixtures of several anionic surfactants without departing from the scope of the invention.

Examples of the nonionic surfactants which may be used in the microemulsion compositions, include ethoxylated di ( 1-phenylethyl )phenols containing from 2 to 50 EO units, propoxylated di(1-phenylethyl)phenols containing from 2 to 50 PO units, ethoxypropoxylated di( 1-phenylethyl )phenols containing from 2 to 50 EO + PO units, ethoxylated tri (1-phenylethyl)phenols containing from 2 to 50 EO units, propoxylated tri(1-phenylethyl) phenols containing from 2 to 50 PO units, ethoxypropoxylated tri(1-phenylethyl)-phenols containing from 2 to 50 EO + PO units, ethoxypropoxylated nonylphenols containing from 2 to 100 EO + PO units and the like.

Examples of nonionic surfactants which may be used in the stable, microemulsion compositions, include, such compounds as ethoxypropoxylated nonylphenols having 25 EO + PO units, ethoxypropoxylated nonylphenols having 30 EO + PO units, ethoxypropoxylated nonylphenols having 40 EO + PO units, ethoxypropoxylated nonylphenols having 55 EO + PO units, ethoxypropoxylated nonylphenols having 80 EO + PO units, ethoxypropoxylated tri(1-phenylethyl)-phenols having 25 EO + PO units, ethoxylated tri ( 1-phenylethyl )phenol having 16 EO units, ethoxylated tri ( 1-phenylethyl )phenol having 20 EO units, ethoxylated tri(1-phenylethyl)phenol having 25 EO units, ethoxylated tri(1-phenylethyl)phenol having 40 EO units, ethoxylated di(1-phenylethyl)phenol having 5 EO units, ethoxylated di ( 1-phenylethyl )phenol having 11 EO units, ethoxylated di( 1-phenylethyl)-phenol having 15 EO units and the like.

As in the case of the anionic surfactants, mixtures of two or more nonionic surfactants may be used without departing from the scope of the invention.

When the anionic surfactant is an alkylbenzenesulfonate as defined above, the nonionic surfactant is preferably chosen from alkoxylated di(1-phenylethyl)phenols and alkoxylated tri(1-phenylethyl) phenols.

The co-surfactants which may be used in the present invention, include, for example, n-butanol, isobutanol (butan-2-ol), n-propanol, isopropanol (propan-2-ol, n-pentanol and its branched isomers, n-hexanol and its branched isomers, cyclopentanol, cyclohexanol, methylcyclohexanols, benzyl alcohol, phenylethyl alcohol, 2-methoxyethanol, 2-ethoxyethanol, 2-isopropoxyethanol, 2-n-butoxyethanol, diethylene glycol monomethyl ether, diethylene glycol monoethyl ether, diethylene glycol mono-n-butyl ether, triethylene glycol monoethyl ether, heptanoic acid and its branched isomers, octanoic acid and its branched isomers, nonanoic acid and its branched isomers, decanoic acid and its branched isomers and the like.

It is possible to use mixtures of co-surfactants, i.e., two or more co-surfactants, as well as one co-surfactant in the compositions of the present invention.

In general, it is preferred to use co-surfactants having a flash point higher than 50° C. The flash point is defined as the temperature above which the vapors of the product ignite spontaneously in contact with a flame.

The lists of surfactants, including anionic surfactants, nonionic surfactants and co-surfactants which are provided above, are not meant to limit the scope of the present invention, and it is within the purview of one skilled in the art, without undue experimentation to provide additional anionic, nonionic and cosurfactants which may be used in the surfactant systems and compositions of the present invention.

In preferred embodiments, the microemulsion compositions according to the invention have from 0.1% to 70% by weight of at least one pyrethroid in liquid form, and from 2% to 50% by weight of a surfactant system comprising at least one anionic surfactant, at least one nonionic surfactant and at least one co-surfactant, in which the ratio by weight of anionic surfactant/nonionic surfactant is from 15/85 to 85/15 and the ratio by weight of cosurfactant/anionic and nonionic surfactants is from 0.25 to 0.80. The microemulsion compositions according to the invention are stable at a temperature range of from −5° C. to +45° C.

The microemulsion compositions according to the invention may contain, in addition to the compounds defined above, other compounds conventionally used in plant protection compositions, such as, for example, anti-foams, such as organopolysiloxanes; thickeners, such as xanthan gum; preservatives; an antigel, such as monopropylene glycol or monoethylene glycol, and the like as well-known in the art.

The preparation of the microemulsion compositions of the invention is not critical, and in preferred embodiments, they are prepared by simple mixing of the various constituents. The microemulsion compositions of the invention do not give rise to any coalescence, crystallization or sedimentation phenomenon on storage.

The microemulsion compositions of the present invention may be used to control insects, in particular in the treatment of crops or the protection of wood, either directly or after dilution with water at the time of their use. On dilution, the microemulsion compositions lead to stable emulsions or remain microemulsions. In the area of plant protection, the dilute emulsions or microemulsions are preferably prepared by the user at the time of use, and thereafter they are not generally stored for more than 24 hours.

In accordance with the present invention, there is also provided a method for controlling insects which attack plants or wood, by applying to the plants or wood, a microemulsion of the pyrethroid microemulsion compositions of the present invention. In a preferred embodiment, the method of the present invention is directed to diluting the microemulsion compositions of the present invention in any desired proportion with water, and applying the emulsion or microemulsion resulting from the dilution with water to the plants or wood. The application of the emulsions or microemulsions prepared as described above, to plants (crops) or to wood, may be by any conventional technique, e.g., by spraying the compositions.

As used herein, the stable pyrethroid microemulsions are in water and therefore, they are aqueous microemulsions.

Unless otherwise stated, as used herein % by weight represents the % weight based on the total weight of the composition.

The present invention is more fully described by means of the following detailed examples which should be considered as illustrative only and non-limiting.

EXAMPLE 1

A microemulsion was prepared by mixing the following compounds, in the amounts shown, by stirring 10.90 g of cypermethrin, 15.34 g of ethoxylated tri(1-phenylethyl)phenol containing 16 EO units, 8.26 g of ethoxylated tri(1-phenylethyl)phenol phosphate containing 16 EO units and neutralized by triethanolamine, 11.80 g of isobutanol, and 53.70 g of water, i.e., sufficient water to make up to 100 g total weight.

A microemulsion was obtained which was clear, fluid and stable when tested under a temperature cycle of −5° C., +45° C.

EXAMPLE 2

Example 1 was repeated by mixing 27.90 g of cypermethrin, 18.64 g of ethoxylated tri(1-phenylethyl)phenol containing 16 EO units, 10.03 g of ethoxylated tri(1-phenylethyl)phenol phosphate containing 16 EO units and neutralized by triethanolamine, 14.33 g of isobutanol, and 29.10 g of water, i.e., sufficient water to make up to 100 g total weight.

A microemulsion was obtained which was clear, fluid and stable when tested under a temperature cycle of −5° C. +45° C.

EXAMPLE 3

Example 1 was repeated by mixing 9.40 g of cypermethrin, 14.26 g of ethoxylated tri(1-phenylethyl)phenol containing 16 EO units, 7.68 g of ethoxylated tri(1-phenylethyl)phenol phosphate containing 16 EO units and neutralized by triethanolamine, 16.46 g of cyclohexanol, and 52.20 g of water, i.e., sufficient water to make up to 100 g total weight.

A microemulsion was obtained which was clear, fluid and stable when tested under a temperature cycle of −5° C. +45° C.

EXAMPLE 4

Example 1 was repeated by mixing 26.10 g of cypermethrin, 25.63 g of ethoxylated tri(1-phenylethyl)phenol containing 16 EO units, 13.80 g of ethoxylated tri(1-phenylethyl)phenol phosphate containing 16 EO units and neutralized by triethanolamine, 29.57 g of cyclohexanol, and 4.90 g of water, i.e., sufficient water to make up to 100 g total weight.

A microemulsion was obtained which was clear, fluid and stable when tested under a temperature cycle of −5° C. +45° C.

EXAMPLE 5

Example 1 was repeated by mixing 9.0 g of cypermethrin, 33.98 g of ethoxylated di(1-phenylethyl)phenol containing 15 EO units, 18.30 g of ethoxylated di(1-phenylethyl)phenol sulfate containing 15 EO units and neutralized by KOH, 26.14 g of isobutanol, and 12.58 g of water, i.e., sufficient water to make up to 100 g total weight.

A microemulsion was obtained which was clear, fluid and stable when tested under a temperature cycle of −5° C., +45° C.

EXAMPLE 6

Example 1 was repeated by mixing 23.0 g of cypermethrin, 25.52 g of ethoxylated di(1-phenylethyl)phenol containing 15 EO units, 13.74 g of ethoxylated di(1-phenylethyl)phenol sulfate containing 15 EO units and neutralized by KOH, 19.64 g of isobutanol, and 18.10 g of water, i.e., sufficient water to make up to 100 g total weight.

A microemulsion was obtained which was clear, fluid and stable when tested under a temperature cycle of −5° C., +45° C.

EXAMPLE 7

Example 1 was repeated by mixing 9.03 g of permethrin, 20.11 g of ethoxylated tri(1-phenylethyl)phenol containing 16 EO units, 10.83 g of ethoxylated tri(1-phenylethyl)phenol phosphate containing 16 EO units and neutralized by triethanolamine, 15.46 g of isobutanol, and 44.57 g of water, i.e., sufficient water to make up to 100 g total weight.

A microemulsion was obtained which was clear, fluid and stable when tested under a temperature cycle of −5° C., +45° C.

EXAMPLE 8

Example 1 was repeated by mixing 26.80 g of permethrin, 18.46 g of ethoxylated tri(1-phenylethyl)phenol containing 16 EO units, 9.94 g of ethoxylated tri(1-phenylethyl)phenol phosphate containing 16 EO units and neutralized by triethanolamine, 14.20 g of isobutanol, and 30.60 g of water, i.e., sufficient water to make up to 100 g total weight.

A microemulsion was obtained which was clear, fluid and stable when tested under a temperature cycle of $-5°$ C., $+45°$ C.

EXAMPLE 9

Example 1 was repeated by mixing 27.60 g of cypermethrin, 22.95 g of ethoxylated tri(1-phenylethyl)phenol containing 16 EO units, 12.36 g of ethoxylated tri(1-phenylethyl)phenol phosphate containing 16 EO units and neutralized by triethanolamine, 26.49 g of cyclohexanol, and 10.60 g of water, i.e., sufficient water to make up to 100 g total weight.

A microemulsion was obtained which was clear, fluid and stable when tested under a temperature cycle of $-5°$ C. $+45°$ C.

EXAMPLE 10

Example 1 was repeated by mixing 8.70 g of deltamethrin, 28.40 g of aromatic petroleum cut (Solvesso 150), 15.20 g of cyclohexanone, 13.50 g of ethoxylated tri(1-phenylethyl)phenol containing 16 EO units, 7.30 g of ethoxylated tri(1-phenylethyl)phenol sulfate containing 16 EO units and neutralized by $NH_3$, 13.90 g of cyclohexanol, 2.60 g monopropylene glycol, and 10.40 g of water, i.e., sufficient water to make up to 100 g total weight.

A microemulsion was obtained which was clear, fluid and stable when tested under a temperature cycle of $-5°$ C., $+45°$ C.

EXAMPLE 11

Example 1 was repeated by mixing 42.30 g of permethrin, 17.16 g of ethoxylated tri(1-phenylethyl)phenol containing 16 EO units, 9.24 g of ethoxylated tri(1-phenylethyl)phenol phosphate containing 16 EO units and neutralized by triethanolamine, 20.0 g of cyclohexanol, and 11.30 g of water, i.e., sufficient water to make up to 100 g total weight.

A microemulsion was obtained which was clear, fluid and stable when tested under a temperature cycle of $-5°$ C., $+45°$ C.

EXAMPLE 12

Example 1 was repeated by mixing 48.6 g of cypermethrin, 15.50 g of ethoxylated tri(1-phenylethyl)phenol containing 16 EO units, 8.30 g of ethoxylated tri(1-phenylethyl)phenol phosphate containing 16 EO units and neutralized by triethanolamine, 18.0 g of cyclohexanol, and 9.60 g of water, i.e., sufficient water to make up to 100 g total weight.

A microemulsion was obtained which was clear, fluid and stable when tested under a temperature cycle of $-5°$ C., $+45°$ C.

EXAMPLE 13

Example 1 was repeated by mixing 45.6 g of cypermethrin, 6.0 g of ethoxylated tri(1-phenylethyl)phenol containing 25 EO units, 24.0 g of ethoxylated tri(1-phenylethyl)phenol phosphate containing 16 EO units and neutralized by triethanolamine, 14.8 g of isobutanol, and 9.6 g of water, i.e., sufficient water to make up to 100 g total weight.

A microemulsion was obtained which was clear, fluid and stable when tested under a temperature cycle of $-5°$ C., $+45°$ C.

EXAMPLE 14

Example 1 was repeated by mixing 47.3 g of cypermethrin, 15.9 g of ethoxylated tri(1-phenylethyl)phenol containing 16 EO units, 10.14 g of ethoxylated tri(1-phenylethyl)phenol sulfate containing 15 EO units and neutralized by KOH, 14.52 g of isobutanol, and 12.14 g of water, i.e., sufficient water to make up to 100 g total weight.

A microemulsion was obtained which was clear, fluid and stable when tested under a temperature cycle of $-5°$ C., $+45°$ C.

EXAMPLE 15

Example 1 was repeated by mixing 47.3 g of cypermethrin, 21.7 g of ethoxylated tri(1-phenylethyl)phenol containing 16 EO units, 13.0 g of calcium dodecylbenzenesulfonate, 8.7 g of isobutanol, and 9.3 g of water i.e., sufficient water to make up to 100 g total weight.

A microemulsion was obtained which was clear, fluid and stable when tested under a temperature cycle of $-5°$ C., $+45°$ C.

EXAMPLE 16

Example 1 was repeated by mixing 28.0 g of cypermethrin, 10.27 g of ethoxylated tri(1-phenylethyl)phenol containing 16 EO units, 19.06 g of ethoxylated tri(1-phenylethyl)phenol phosphate containing 16 EO units and neutralized by KOH, 14.67 g of isobutanol, and 28.09 g of water, i.e., sufficient water to make up to 100 g total weight.

A microemulsion was obtained which was clear, fluid and stable when tested under a temperature cycle of $-5°$ C., $+45°$ C.

EXAMPLE 17

Example 1 was repeated by mixing 28.0 g of cypermethrin, 10.27 g of ethoxylated tri(1-phenylethyl)phenol containing 16 EO units, 19.06 g of ethoxylated tri(1-phenylethyl)phenol phosphate containing 16 EO units and neutralized by $NH_3$, 14.67 g of isobutanol, and 28.0 g of water, i.e., sufficient water to make up to 100 g total weight.

A microemulsion was obtained which was clear, fluid and stable when tested under a temperature cycle of $-5°$ C., $+45°$ C.

COMPARATIVE EXPERIMENT A

Example 1 (similar to Example 17) was repeated by mixing 28.0 g of cypermethrin, 10.27 of ethoxylated tri(1-phenylethyl)phenol containing 16 EO units, 19.06 g of ethoxylated tri(1-phenylethyl)phenol phosphate containing 16 EO units in acid form, 14.67 g of isobutanol, and 28.0 g of water, i.e., sufficient water to make up to 100 g total weight.

A microemulsion was obtained which was clear, fluid and stable when tested at 20° C. but unstable when it was subjected to heat cycles in the temperature zone of $-5°$ C., $+45°$ C.

EXAMPLE 18

Example 1 was repeated by mixing 58.0 g of cypermethrin, 8.17 g of ethoxylated tri ( 1-phenylethyl ) phenol containing 16 EO units, 15.16 g of ethoxylated tri(1-phenylethyl )phenol phosphate containing 16 EO units and neutralized by KOH, 11.67 g of isobutanol, and 7.0 g of water, i.e., sufficient water to make up to 100 g total weight.

A microemulsion was obtained which was clear, fluid and stable when tested under a temperature cycle of $-5°$ C. $+45°$ C.

EXAMPLE 19

Example 1 was repeated by mixing 58.0 g of cypermethrin, 8.17 g of ethoxylated tri(1-phenylethyl)phenol containing 16 EO units, 15.16 g of ethoxylated tri(1-phenylethyl)phenol phosphate containing 16 EO units and neutralized by $NH_3$, 11.67 g of isobutanol, and 7.0 g of water, i.e., sufficient water to make up to 100 g total weight.

A microemulsion was obtained which was clear, fluid and stable when tested under a temperature cycle of $-5°$ C., $+45°$ C.

COMPARATIVE EXPERIMENT B

Example 1 (similar to Example 19) was repeated by mixing 58.0 g of cypermethrin, 8.17 g of ethoxylated tri(1-phenylethyl)phenol containing 16 EO units, 15.16 g of ethoxylated tri(1-phenylethyl)phenol phosphate containing 16 EO units in acid form, 11.67 g of isobutanol, and 7.0 g of water, i.e., sufficient water to make up to 100 g total weight.

A microemulsion was obtained which was clear, fluid and stable when tested at 20° C. but unstable when it was subjected to heat cycles in the temperature zone of $-5°$ C., $+45°$ C.

EXAMPLE 20

Example 1 was repeated by mixing 8.0 g of cypermethrin, 7.23 g of ethoxylated tri(1-phenylethyl)phenol containing 16 EO units, 13.43 g of ethoxylated tri ( 1-phenylethyl )phenol phosphate containing 16 EO units and neutralized by KOH, 10.34 g of isobutanol, and 61.0 g of water, i.e., sufficient water to make up to 100 g total weight.

A microemulsion was obtained which was clear, fluid and stable when tested under a temperature cycle of $-5°$ C., $+45°$ C.

EXAMPLE 21

Example 1 was repeated by mixing 8.0 g of cypermethrin, 7.23 g of ethoxylated tri ( 1-phenylethyl )phenol containing 16 EO units, 13.43 g of ethoxylated tri( 1-phenylethyl )phenol phosphate containing 16 EO units and neutralized by $NH_3$, 10.34 g of isobutanol, and 61.0 g of water, i.e., sufficient water to make up to 100 g total weight.

A microemulsion was obtained which was clear, fluid and stable when tested under a temperature cycle of $-5°$ C., $+45°$ C.

COMPARATIVE EXPERIMENT C

Example 1 (similar to Example 21) was repeated by mixing 8.0 g of cypermethrin, 7.23 of ethoxylated tri(1-phenylethyl)phenol containing 16 EO units, 13.43 g of ethoxylated tri(1-phenylethyl)phenol phosphate containing 16 EO units in acid form, 10.34 g of isobutanol, and 61.0 g of water, i.e., sufficient water to make up to 100 g total weight.

A microemulsion was obtained which was clear, fluid and stable when tested at 20° C. but unstable when it was subjected to heat cycles in the temperature zone of $-5°$ C., $+45°$ C.

EXAMPLE 22

Example 1 was repeated by mixing 8.0 g of cypermethrin, 10.13 g of ethoxylated tri(1-phenylethyl)phenol containing 16 EO units, 10.13 g of ethoxylated tri( 1-phenylethyl )phenol sulfate containing 16 EO units and neutralized by $NH_3$, 10.13 g of isobutanol, and 61.61 g of water, i.e., sufficient water to make up to 100 g total weight.

A microemulsion was obtained which was clear, fluid and stable when tested under a temperature cycle of $-5°$ C., $+45°$ C.

COMPARATIVE EXPERIMENT D

Example 1 (similar to Example 22) was repeated by mixing 8.0 g of cypermethrin, 10.13 g of ethoxylated nonylphenol containing 10 EO units, 10.13 g of ethoxylated tri(1-phenylethyl)phenol sulfate containing 16 EO units and neutralized by $NH_3$, 10.13 g of isobutanol, and 61.61 g of water, i.e., sufficient water to make up to 100 g total weight.

A microemulsion was obtained which was clear, fluid and stable when tested at 20° C. but unstable when it was subjected to heat cycles in the temperature zone of $-5°$ C., $+45°$ C.

COMPARATIVE EXPERIMENT E

Example 1 (similar to Example 22) was repeated by mixing 8.0 g of cypermethrin, 10.13 g of ethoxylated nonylphenol containing 17 EO units, 10.13 g of ethoxylated tri(1-phenylethyl)phenol sulfate containing 16 EO units and neutralized by $NH_3$, 10.13 g of isobutanol, and 61.61 g of water, i.e., sufficient water to make up to 100 g total weight.

A microemulsion was obtained which was clear, fluid and stable when tested at 20° C. but unstable when it was subjected to heat cycles in the temperature zone of $-5°$ C., $+45°$ C.

EXAMPLE 23

Example 1 was repeated by mixing 28.0 g of cypermethrin, 14.67 g of ethoxylated tri(1-phenylethyl)phenol containing 16 EO units, 14.67 g of ethoxylated tri(1-phenylethyl)phenol sulfate containing 16 EO units and neutralized by $NH_3$, 14.66 g of isobutanol, and 28.0 g of water, i.e., sufficient water to make up to 100 g total weight.

A microemulsion was obtained which was clear, fluid and stable when tested under a temperature cycle of $-5°$ C., $+45°$ C.

COMPARATIVE EXPERIMENT F

Example 1 (similar to Example 23) was repeated by mixing 28.0 g of cypermethrin, 14.67 g of ethoxylated nonylphenol containing 10 EO units, 14.67 g of ethoxylated tri(1-phenylethyl)phenol sulfate containing 16 EO units and neutralized by $NH_3$, 14.66 g of isobutanol, and 28.0 g of water, i.e., sufficient water to make up to 100 g total weight.

A microemulsion was obtained which was clear, fluid and stable when tested at 20° C. but unstable when it was subjected to heat cycles in the temperature zone of −5° C., +45° C.

Other embodiments of the invention will be apparent to those skilled in the art from consideration of the specification and practice of the invention disclosed herein. It is intended that the specification and examples be considered as exemplary only, with the scope and spirit of the invention being indicated by the following claims.

What is claimed is:

1. A stable pyrethroid microemulsion composition comprising:
   (1) from 0.1% to 95% by weight/weight of at least one synthetic pyrethroid in liquid form:
   (2) from 2% to 90% by weight/weight of a surfactant system comprising:
      (a) at least one anionic surfactant selected from the group consisting of neutral phosphates or sulfates of ethoxylated, propoxylated or ethoxypropoxylated di(1-phenylethyl)phenols and ethoxylated, propoxylated or ethoxypropoxylated tri(1-phenylethyl) phenols;
      (b) at least one nonionic surfactant selected from the group consisting of ethoxylated, propoxylated or ethoxypropoxylated di(1-phenylethyl)phenols, ethoxylated, propoxylated, propoxylated or ethoxypropoxylated tri(1-phenylethyl)phenols and ethoxypropoxylated nonylphenols; and
      (c) at least one co-surfactant selected from the group consisting of straight-chain or branched aliphatic alcohols having from 3 to 10 carbon atoms, cycloaliphatic alcohols having from 5 to 12 carbon atoms, arylaliphatic alcohols having from 7 to 12 carbon atoms, ether-alcohols of the formula R-(OR')$_n$-OH, wherein R represents a straight-chain or branched alkyl radical having from 1 to 8 carbon atoms; R' represents an alkylene radical; and n represents an integer from 1 to 3; and straightchain or branched aliphatic carboxylic acids having from 5 to 10 carbon atoms; and
   (3) water;
wherein the ratio by weight of anionic surfactant/nonionic surfactant is from 10.90 to 90/10, and the ratio by weight of cosurfactant/anionic surfactants is from 0.25 to 0.80.

2. The pyrethroid microemulsion composition according to claim 1, wherein the pyrethroids are insecticidal compounds selected from the group consisting of allethrin, bifenthrin, bioallethrin, bioresmethrin, cyfluthrin, cyhallothrin, cypermethrin, deltamethrin, fenpropathrin, permethrin, phenothrin, pyrethrins, resmethrin, tefluthrin, tetramethrin, tralomethrin and (E)-5-benzyl-3-furylmethyl-(1R)-cis-2,2-dimethyl-3-(2-oxothiolan-3-ylidenemethyl)cyclopropanecarboxylate.

3. The pyrethroid microemulsion composition according to claim 1, wherein the pyrethroids are liquid at ambient temperature or may be supercooled.

4. The pyrethroid microemulsion composition according to claim 1, wherein the pyrethroids are in solution in an organic solvent, said solvent being insoluble in water.

5. The pyrethroid microemulsion composition according to claim 4, wherein the organic solvent, enabling the pyrethroids to be maintained in the liquid state, is selected from the group consisting of aromatic hydrocarbons, aromatic petroleum cuts; fatty acid alkyl esters, dialkyl phthalates, chlorinated hydrocarbons, and cyclic ketones.

6. The pyrethroid microemulsion composition according to claim 5, wherein the aromatic hydrocarbon is selected from the group consisting of benzene, toluene and xylene; wherein the fatty acid alkyl ester is methyl oleate; wherein the dialkyl phthalate is di(2-ethylhexy) phthalate; wherein the chlorinated hydrocarbon is selected from the group consisting of dichloromethane, trichloromethane and 1,2-chloroethane; and wherein the cyclic ketone is selected from the group consisting of cyclopentanone, cyclohexanone and isophorone.

7. The pyrethroid microemulsion composition according to claim 4, wherein the ratio by weight of organic solvent/pyrethroid varies from 5/95 to 90/10.

8. The pyrethroid microemulsion composition according to claim 1, wherein the anionic surfactants are selected from the group consisting of phosphoric monoesters of ethoxylated di(1-phenylethyl)phenols containing from 2 to 50 ethylene oxide (EO) units, phosphoric diesters of ethoxylated di(1-phenylethyl)phenols containing 2 to 50 EO units, phosphoric monoesters of ethoxylated tri(1-phenylethyl)phenols containing from 2 to 50 EO units, phosphoric diesters of ethoxylated tri(1-phenylethyl)phenols containing from 2 to 50 EO units, phosphoric monoesters of propoxylated di(1-phenylethyl)phenols containing from 2 to 50 propylene oxide (PO) units, phosphoric diesters of propoxylated di(1-phenylethyl)phenols containing from 2 to 50 PO units, phosphoric monoesters of propoxylated tri(1-phenylethyl)phenols containing from 2 to 50 PO units, phosphoric diesters of propoxylated tri(1-phenylethyl)phenols containing from 2 to 50 PO units, phosphoric monoesters of ethoxypropoxylated di(1-phenylethyl)phenols containing from 2 to 50 EO + PO units, phosphoric diesters of ethoxypropoxylated di(1-phenylethyl)phenols containing from 2 to 50 EO + PO units, phosphoric monoesters of ethoxypropoxylated tri(1-phenylethyl)phenols containing from 2 to 50 EO + PO units, phosphoric diesters of ethoxypropoxylated tri(1-phenylethyl) phenols containing from 2 to 50 EO + PO units, sulfuric monoesters of ethoxylated di(1-phenylethyl) phenols containing from 2 to 50 EO units, sulfuric diesters of ethoxylated di(1-phenylethyl)phenols containing from 2 to 50 EO units, sulfuric monoesters of propoxylated di(1-phenylethyl)phenols containing from 2 to 50 PO units, sulfuric diesters of propoxylated di(1-phenylethyl)phenols containing from 2 to 50 PO units, sulfuric monoesters of ethoxypropoxylated di(1-phenylethyl)phenols containing from 2 to 50 EO + PO units, sulfuric diesters of ethoxypropoxylated di(1-phenylethyl)phenols containing from 2 to 50 EO + PO units, sulfuric monoesters of ethoxylated tri(1-phenylethyl)phenols containing from 2 to 50 EO units, sulfuric diesters of ethoxylated tri(1-phenylethyl)phenols containing from 2 to 50 EO units, sulfuric monoesters of propoxylated tri(1-phenylethyl)phenols containing from 2 to 50 PO units, sulfuric diesters of propoxylated tri(1-phenylethyl)phenols containing from 2 to 50 PO units, sulfuric monoesters of ethoxypropoxylated tri(1-phenylethyl)phenols containing from 2 to 50 EO + PO units, and sulfuric diesters of ethoxypropoxylated tri(1-phenylethyl)phenols containing from 2 to 50 EO + PO units, the free acid functions being neutralized by compounds selected from the group consisting of alkanolamines, ammonium cations, potassium cations, and sodium cations.

9. The pyrethroid microemulsion composition according to claim 1, wherein the anionic surfactants are selected from the group consisting of triethanolamine salts of the phosphoric monoester of ethoxylated tri(1-phenylethyl)phenol containing 16 EO units, triethanolamine salts of the phosphoric diester of ethoxylated tri(1-phenylethyl)phenol containing 16 EO units, the potassium salts of the phosphoric monoester of ethoxylated tri(1-phenylethyl)phenol containing 16 EO units, the potassium salts of the phosphoric diester of ethoxylated tri(1-phenylethyl)phenol containing 16 EO units, the potassium salt of the sulfuric monoester of the ethoxylated di(1-phenylethyl)phenol containing 15 EO units, the triethanolamine salt of the sulfuric monoester of ethoxylated di(1-phenylethyl)phenol containing 11 EO units, the ammonium salt of the sulfuric monoester of ethoxylated tri(1-phenylethyl)phenol containing 16 EO units, the ammonium salt of the sulfuric monoester of ethoxylated di(1-phenylethyl)phenol containing 5 EO units, the ammonium salt of the sulfuric monoester of ethoxylated di(1-phenylethyl)phenol containing 7 EO units, and the ammonium salt of the sulfuric monoester of ethoxylated di(1-phenylethyl)phenol containing 11 EO units.

10. The pyrethroid microemulsion composition according to claim 1, wherein the nonionic surfactants are selected from the group consisting of ethoxylated di(1-phenylethyl)phenols containing from 2 to 50 EO units, propoxylated di(1-phenylethyl)phenols containing from 2 to 50 PO units, ethoxypropoxylated di(1-phenylethyl)phenols containing from 2 to 50 EO + PO units, ethoxylated tri(1-phenylethyl)phenols containing from 2 to 50 EO units, propoxylated tri(1-phenylethyl)phenols containing from 2 to 50 PO units, ethoxypropoxylated tri(1-phenylethyl)phenols containing from 2 to 50 EO + PO units, and ethoxypropoxylated nonylphenols containing from 2 to 100 EO + PO units.

11. The pyrethroid microemulsion composition according to claim 1, wherein the nonionic surfactants are selected from the group consisting of ethoxypropoxylated nonylphenols having 25 EO + PO units, ethoxypropoxylated nonylphenols having 30 EO + PO units, ethoxypropoxylated nonylphenols having 40 EO + PO units, ethoxypropoxylated nonylphenols having 55 EO + PO units, ethoxypropoxylated nonylphenols having 80 EO + PO units, ethoxypropoxylated tri(1-phenylethyl)phenols having 25 EO + PO units, ethoxylated tri(1-phenylethyl)phenol having 16 EO units, ethoxylated tri(1-phenylethyl)phenol having 20 EO units, ethoxylated tri(1-phenylethyl)phenol having 25 EO units, ethoxylated tri(1-phenylethyl)phenol having 40 EO units, ethoxylated di(1-phenylethyl)phenol having 5 EO units, ethoxylated di(1-phenylethyl)phenol having 11 EO units, and ethoxylated di(1-phenylethyl)phenol having 15 EO units.

12. The pyrethroid microemulsion composition according to claim 1, wherein the co-surfactants are selected from the group consisting of n-butanol, isobutanol, n-propanol, isopropanol, n-pentanol and its branched isomers, n-hexanol and its branched isomers, cyclopentanol, cyclohexanol, methylcyclohexanols, benzyl alcohol, phenylethyl alcohol, 2-methoxyethanol, 2-ethoxyethanol, 2-isopropoxyethanol, 2-n-butoxyethanol, diethylene glycol monomethyl ether, diethylene glycol monoethyl ether, diethylene glycol mono-n-butyl ether, triethylene glycol monoethyl ether, heptanoic acid and its branched isomers, octanoic acid and its branched isomers, nonanoic acid and its branched isomers and decanoic acid and its branched isomers.

13. The pyrethroid microemulsion composition according to claim 1, comprising from 0.1% to 70% by weight of at least one pyrethroid in liquid form, and from 2% to 50% by weight of a surfactant system comprising at least one anionic surfactant, at least one nonionic surfactant and at least one co-surfactant, wherein the ratio by weight of anionic surfactant/nonionic surfactant is from 15/85 to 85/15 and the ratio by weight of cosurfactant/anionic and nonionic surfactants is from 0.25 to 0.80.

14. The pyrethroid microemulsion composition according to claim 1, wherein the microemulsion is clear, fluid and stable at a temperature cycle of −5° C., +45° C.

15. A method for controlling insects which attack plants or wood, comprising application of the pyrethroid microemulsion composition of claim 1 to the plants or the wood.

16. The method of claim 15, further comprising diluting the pyrethroid microemulsion with water to form a diluted pyrethroid emulsion or microemulsion, and thereafter applying the diluted emulsion or microemulsion to the plants or wood.

17. The method of claim 15, wherein the pyrethroid microemulsion composition is applied by spraying the aqueous emulsion.

18. The method of claim 15 wherein the pyrethroids are insecticidal compounds selected from the group consisting of allethrin, bifenthrin, bioallethrin, bioresmethrin, cyfluthrin, cyhallothrin, cypermethrin, deltamethrin, fenpropathrin, permethrin, phenothrin, pyrethrins, resmethrin, tefluthrin, tetramethrin, tralomethrin and (E)-5-benzyl-3-furylmethyl-( 1R )-cis- 2, 2-dimethyl- 3- ( 2-oxothiolan- 3-ylidenemethyl ) cyclopropanecarboxylate.

19. The method of claim 15 wherein the pyrethroid microemulsion composition comprises from 0.1% to 70% by weight of at least one pyrethroid in liquid form, and from 2% to 50% by weight of a surfactant system comprising at least one anionic surfactant, at least one nonionic surfactant and at least one cosurfactant, wherein the ratio by weight of anionic surfactant/nonionic surfactant is from 15/85 to 85/15 and the ratio by weight of co-surfactant/anionic and nonionic surfactants is from 0.25 to 0.80.

* * * * *

UNITED STATES PATENT AND TRADEMARK OFFICE
CERTIFICATE OF CORRECTION

PATENT NO. : 5,334,585  
DATED : August 02, 1994  
INVENTOR(S) : Paul-Joel DERIAN et al.

It is certified that error appears in the above-indentified patent and that said Letters Patent is hereby corrected as shown below:

Claim 1, column 11, lines 26-27, change "propoxylated propoxylated" to --propoxylated--.

Claim 1, column 11, line 40, change "straightchain" to --straight-chain--.

Claim 1, column 11, line 45, change "10.90" to --10/90--.

Signed and Sealed this

Twenty-eight Day of February, 1995

Attest:

BRUCE LEHMAN

Attesting Officer

Commissioner of Patents and Trademarks